United States Patent
Azuma et al.

[11] Patent Number: 6,093,679
[45] Date of Patent: Jul. 25, 2000

[54] EFFICACY ENHANCER FOR AGRICULTURAL CHEMICALS AND AGRICULTURAL CHEMICAL COMPOSITIONS

[75] Inventors: Toshikazu Azuma; Tadayuki Suzuki; Keiko Hasebe, all of Wakayama, Japan

[73] Assignee: Kao Corporation, Tokyo, Japan

[21] Appl. No.: 08/913,049

[22] PCT Filed: Feb. 26, 1997

[86] PCT No.: PCT/JP97/00558

§ 371 Date: Sep. 5, 1997

§ 102(e) Date: Sep. 5, 1997

[87] PCT Pub. No.: WO97/31527

PCT Pub. Date: Sep. 4, 1997

[30] Foreign Application Priority Data

Mar. 1, 1996 [JP] Japan ................................. 8-045174

[51] Int. Cl.⁷ ............................ A01N 33/04; A01N 31/02
[52] U.S. Cl. ...................... 504/116; 252/352; 252/356; 252/357; 424/405; 504/171; 504/172; 514/784; 514/785; 514/788
[58] Field of Search ........................ 504/116, 171, 504/172; 514/784, 785, 946, 788; 554/63, 64; 252/352, 356, 357

[56] References Cited

U.S. PATENT DOCUMENTS

| | | | |
|---|---|---|---|
| 3,775,052 | 11/1973 | Van Paassen | 8/137 |
| 4,834,908 | 5/1989 | Hazen et al. | 252/356 |
| 4,865,757 | 9/1989 | Singh-Verma et al. | 252/117 |
| 5,622,911 | 4/1997 | Hasbe et al. | 504/116 |

FOREIGN PATENT DOCUMENTS

| | | |
|---|---|---|
| 2716075 | 8/1995 | France . |
| 1260061 | 2/1968 | Germany . |
| 2-155994 | 6/1990 | Japan . |
| 647929 | 2/1985 | Switzerland . |
| 9517817 | 7/1995 | WIPO . |
| 9531903 | 11/1995 | WIPO . |

OTHER PUBLICATIONS

Abe et al, J of American Oil Chemists' Society, vol. 46, pp 865–867, 1969.

*Primary Examiner*—Shailendra Kumar
*Attorney, Agent, or Firm*—Birch, Stewart, Kolasch & Birch, LLP

[57] ABSTRACT

An efficacy enhancer for agricultural chemicals and an agricultural chemical composition are disclosed which each manifest perfect stability even when they are incorporated into given agricultural chemicals at high concentrations and which possess excellent efficacy enhancing actions.

A compound of the following formula (I) is used as the efficacy enhancer.

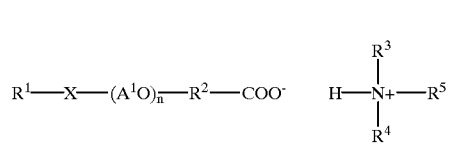

(I)

26 Claims, No Drawings

EFFICACY ENHANCER FOR AGRICULTURAL CHEMICALS AND AGRICULTURAL CHEMICAL COMPOSITIONS

This application is a 371 of PCT/SP97/00558, filed Feb. 26, 1997.

FIELD OF THE INVENTION

This invention relates to a novel efficacy enhancer for agricultural chemicals, an efficacy enhancing composition for agricultural chemicals, and agricultural chemical compositions containing them.

PRIOR ART

The agricultural chemicals including insecticides, bactericides, herbicides, acaricides, and plant growth regulators are used in such forms as emulsifiable concentrates (emulsions), wettable powders, granules, dusts, flowable powders, and liquids. Various devices pertaining to agricultural properties have been proposed for the purpose of thoroughly eliciting the effects of such agricultural chemicals. With all the latest techniques, however, it is difficult to further enhance the efficacy of the agricultural chemicals by virtue of a agricultural device. Since it is still more difficult to develop novel agricultural chemicals, the act of enabling the existing agricultural chemicals to manifest an enhanced activity is immensely significant from the industrial point of view.

It has been well known that various surfactants are utilized as an efficacy enhancer for agricultural chemicals. It is known, for example, that the combination of an anionic surfactant with a chelating agent affords a composition which is highly effective in bipyridinium type herbicides (WO95/31903). It is also known that a highly effective efficacy enhancer for agricultural chemicals is obtained by combining a cationic surfactant with a chelating agent and subsequently incorporating another surfactant in the resultant mixture (WO95/17817).

It is further known that an alkyl or alkenyl polyoxyalkylene ether acetic salt is highly effective. When this salt is combined with an additive such as, for example, a chelating agent, a thickener, and an inorganic substance, the stability is degraded so much as to render formulation of the combination extremely difficult. Thus, the combination has never been reduced to practice. Particularly, this degradation of the stability is conspicuous when the salt is incorporated at a high concentration into the combination. Further, the alkyl or alkenyl polyoxyalkylene ether acetate has so high an acidity (pH 2) that it may be dangerous in use and that, in the formulation of an agricultural chemical, it may possibly decompose other surfactants as well as the agricultural chemical itself and degrades the activity of the formulation as well.

SUMMARY OF THE INVENTION

The present inventors have continued a diligent study in search of an efficacy enhancer for agricultural chemicals which, when used in combination with an agricultural chemical, increases or enhances the efficacy of the agricultural chemical. They have consequently found that alkyl or alkenyl amine salts of specific alkyl or alkenylpolyoxyalkylene ether carboxylic acids manifest a particularly strong efficacy enhancing activity to various agricultural chemicals. This invention has been perfected as a result.

Specifically, this invention is directed to providing an efficacy enhancer for agricultural chemical, which comprises a compound of the general formula (I):

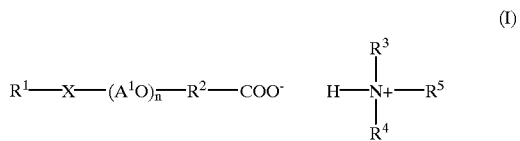

wherein X is —O— or —CONH—; $R^1$ is a linear or a branched alkyl group of 6–20 carbon atoms, a linear or a branched alkenyl group of 6–20 carbon atoms, or an alkylphenyl group containing an alkyl group of 6–18 carbon atoms; $R^2$ is an alkylene group of 1–4 carbon atoms; $R^3$, $R^4$ and $R^5$ are the same or different from each another and at least one of $R^3$, $R^4$ and $R^5$ is selected from the group consisting of a linear or a branched alkyl group of 6–30 carbon atoms and a linear or a branched alkenyl group of 6–30 carbon atoms, and the remainder of $R^3$, $R^4$ and $R^5$ are selected from the group consisting of a benzyl group, hydrogen, and —$(A^2O)_m$—H; $A^1$ and $A^2$ are independently an alkylene group of 2–4 carbon atoms, n is a number of 1–30 on the average, and m is a number of 1–15 on the average.

This invention further concerns the efficacy enhancer mentioned above, wherein X is —O—; $R^1$ is a linear or a branched alkyl group of 6–20 carbon atoms, a linear or a branched alkenyl group of 6–20 carbon atoms, or an alkylphenyl group containing an alkyl group of 6–18 carbon atoms; and at least one of $R^3$, $R^4$ and $R^5$ is a linear or a branched alkyl group of 6–30 carbon atoms and the remainder of $R^3$, $R^4$ and $R^5$ are selected from the group consisting of a benzyl group, hydrogen, and —$(A^2O)_m$—H, wherein $A^2$ and m are defined above.

This invention further concerns the efficacy enhancer described above, wherein $R^3$ is a linear or a branched alkyl group of 6–30 carbon atoms or a linear or a branched alkenyl group of 6–30 carbon atoms; and $R^4$ and $R^5$ are independently a —$(A^2O)_m$—H, wherein $A^2$ and m are defined above.

This invention further concerns the efficacy enhancer described above, wherein $A^1$ is an alkylene group of 2 or 3 carbon atoms or a mixture of alkylene groups of 2 and 3 carbon atoms.

This invention further concerns the efficacy enhancer described above, wherein $R^2$ is an alkylene group of 1 or 2 carbon atoms, and preferably $R^1$ is a linear alkyl group or alkenyl group of 8–18 carbon atoms, $A^1$ is an alkylene group of 2 carbon atoms, $R^2$ is an alkylene group of 1 carbon atom, n is a numeral of 1–10 on the average, $R^3$ is an alkyl group or alkenyl group of 8–20 carbon atoms, $R^4$ and $R^5$ are independently —$(A^2O)_m$—H, $A^2$ is an alkylene group of 2 carbon atoms, and m is a numeral of 1–10 on the average.

This invention is directed to an aqueous efficacy enhancing composition for agricultural chemicals, which comprises at least 20 percent by weight of the efficacy enhancer mentioned above. To be specific, this is a mixture of the efficacy enhancer with water.

This invention is directed to an efficacy enhancing composition for agricultural chemicals, which comprises (a) the compound of the general formula (I) mentioned above and (b) 0.05 to 15 moles, per mole of the compound (a), of a chelating agent.

This invention is directed to an efficacy enhancing composition for agricultural chemicals, which comprises (a) the compound of the general formula (I) mentioned above and (c) at least one surfactant other than the compound of formula (I).

This invention is directed to an efficacy enhancing composition for agricultural chemicals, which comprises (a) the compound of the general formula (I) described above, (c) at least one surfactant other than the compound of formula (I), and (b) 0.05 to 15 moles, per mole of the compound (a), of a chelating agent.

This invention also concerns the composition described above, wherein the surfactant is a non-ionic surfactant.

This invention also concerns the composition described above, wherein the weight ratio of (a) to (c) is in the range of 1:10 to 30:1.

This invention is directed to an agricultural chemical composition, which comprises (a) the compound of the general formula (I) described above and an agricultural chemical, the weight ratio of the compound of formula (I) to the agricultural chemical being in the range of 0.03:1 to 50:1.

This invention also concerns the agricultural chemical composition described above, wherein the agricultural chemical is a bactericide (or fungicide), an insecticide, an acaricide, a herbicide, or a plant-growth regulator.

This invention also concerns the agricultural chemical composition described above, wherein the agricultural chemical is a herbicide.

This invention also concerns the agricultural chemical composition described above, which further comprises (b) a chelating agent.

This invention also concerns the agricultural chemical composition described above, which further comprises (c) at least one surfactant other than the compound of the general formula (I) described above.

This invention is directed to a method for enhancing the efficacy of agricultural chemicals, which comprises applying the efficacy enhancer described above in combination with the agricultural chemicals to a site will benefit from the treatment with the agricultural chemical.

The enhancer of the invention includes compounds in which X is —CONH—, in particular X is —CONH— and $R_1$ is a $C_{7-17}$ alkyl group or a $C_{7-17}$ alkenyl group.

It is preferable that $R_1$—X— is $C_{12}$ alkyl—O— or $C_{11}$ alkyl—CONH—.

DETAILED DESCRIPTION OF THE PREFERRED EMBODIMENTS

The efficacy enhancer of the present invention for an agricultural chemical which comprises a compound of the general formula (I), when used in combination with an agricultural chemical, can exalt the activity of the agricultural chemical from two to three times its original level of activity.

The mechanism by which the efficacy enhancer of the present invention using the compound of the general formula (I), as an active component, manifests the conspicuous efficacy enhancing action to an agricultural chemical without reference to the kind or structure of the agricultural chemical, has not yet been fully elucidated. This conspicuous action may be logically explained by a supposition that since the efficacy enhancer of the present invention shows a very strong solubilizing power to agricultural chemicals, it finely pulverizes the agricultural chemical particles and promotes the permeation of the agricultural chemical thereof into plants, insects, or bacteria.

The precursor (acid type compound) of the compound of the general formula (I) contemplated by this invention prior to the below mentioned treatment is a very strong acid (about pH 2) as mentioned above. When it is included in a composition, therefore, it can decompose the surfactant, the agricultural chemical itself which are used additionally in the composition. When this precursor has been used, therefore, it is generally in the form of salts with Na, K, $NH_3$, and lower alkanol amines (such as mono-, di-, and triethanolamines). When these salts are used at high concentrations, they do not allow for easy handling because they assume high viscosities and undergo gelation. When they take part in the formulation of a composition, they do not prove appropriate from the viewpoint of cost because they cannot be incorporated at a high concentration in the composition.

In contrast to the general practice, this invention elicits the excellent efficacy enhancing effect by relying on the cationic moiety of the compound of the general formula (I) to form the salt of the precursor with the anionic moiety and also enables the compound to be used at a high concentration with high efficiency in the formulation of an agricultural chemical with low viscosity.

The chelating agent (b) to be used in this invention is not particularly limited so long as it possesses the ability to chelate a metal ion. As examples of the chelating agent to be used in this invention, aminopolycarboxylic acid-based chelating agents, aromatic and aliphatic carboxylic acid-based chelating agents, amino acid-based chelating agents, ether polycarboxylic acid-based chelating agents, iminodimethyl phosphoric acid (IDP), alkyl diphosphoric acid (ADPA), and other similar phosphoric acid-based chelating agents, hydroxycarboxylic acid-based chelating agents, phosphoric acid-based chelating agents, macromolecular electrolyte (including oligomer electrolyte)-based chelating agents, and dimethylglyoxime (DG) may be cited. These chelating agents may be in their free acid forms or in the form of such salts as sodium, potassium, and ammonium salts. Alternatively, they may be in the form of their hydrolyzable ester derivatives. The chelating agent is incorporated at a proportion in the range of 0.05 to 15 moles, per mole of the compound of the general formula (I) in the efficacy enhancer of an agricultural chemical.

As examples of the aminopolycarboxylic acid-based chelating agent, a) compounds represented by the chemical formula, $RNY_2$, b) compounds represented by the chemical formula, $NY_3$, c) compounds represented by the chemical formula, R-NY-$CH_2CH_2$-NY-R, d) compounds represented by the chemical formula, R-NY-$CH_2CH_2$-$NY_2$, e) compounds represented by the chemical formula, $Y_2$N-R'-$NY_2$, and f) compounds showing analogy to the compounds of e) while having 4 or more Y's such as, for example, the compounds represented by the formula,

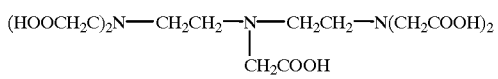

may be cited.

In the formulas mentioned above, Y or $Y_2$ or $Y_3$ is either —$CH_2COOH$ or —$CH_2CH_2COOH$, R is any of such groups as hydrogen atom, alkyl group, hydroxyl group, and hydroxyalkyl group which form known chelating agents of this class, and R' is any of such groups as alkylene group and cycloalkylene group which form known chelating agents of this class.

As typical examples of the aminopolycarboxylic acid-based chelating agent, ethylenediaminetetraacetic acid (EDTA), cyclohexanediaminetetraacetic acid (CDTA), nitrilotriacetic acid (NTA), iminodiacetic acid (IDA), N-(2-hydroxyethyl)-imino-diacetic acid (HIMDA), diethylenetri-aminepentaacetic acid (DTPA), N-(2-hydroxyethyl) ethylenediaminetriacetic acid (EDTA-OH), and glycoletherdiaminetetraacetic acid (GEDTA), and salts thereof may be cited.

Examples of the aromatic and aliphatic carboxylic acid-based chelating agents to be used in this invention include oxalic acid, malonic acid, succinic acid, glutaric acid, adipic acid, itaconic acid, aconitic acid, pyruvic acid, salicylic acid, acetylsalicylic acid, hydroxybenzoic acid, aminobenzoic acid (including anthranilic acid), phthalic acid, trimellitic acid, and gallic acid, salts, methyl esters, and ethyl esters thereof Examples of the amino acid-based chelating agents to be used in this invention include glycine, serine, alanine, lysine, cystine, cysteine, ethionine, tyrosine, methionine, and salts and derivatives thereof.

Further, examples of the ether polycarboxylic acid-based chelating agent to be used in this invention include diglycolic acid, compounds represented by the following formula, compounds analogous thereto, and salts thereof (such as, for example, sodium salt).

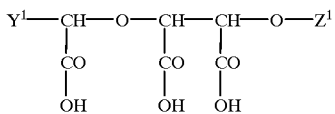

wherein $Y^1$ represents a hydrogen atom, $-CH_2COOH$, or $-COOH$ and $Z^1$ represents a hydrogen atom, $-CH_2COOH$, or

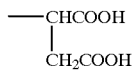

Examples of the hydroxycarboxylic acid-based chelating agent to be used in this invention include malic acid, citric acid, glycolic acid, gluconic acid, heptoic acid, tartaric acid, lactic acid, and salts thereof.

Examples of the phosphoric acid-based chelating agent to be used in this invention include orthophosphoric acid, pyrophosphoric acid, triphosphoric acid, and polyphosphoric acid.

Examples of the macromolecular electrolyte (including oligomer electrolyte)-based chelating agent to be used in this invention include acrylic acid polymer, maleic anhydride polymer, α-hydroxy acrylic acid polymer, itaconic acid polymer, and copolymers formed from two or more of these polymers as component monomers, and epoxy succinic acid polymer.

In addition, ascorbic acid, thioglycolic acid, phytic acid, glyoxylic acid, glyoxalic acid, and salts thereof can be used advantageously as chelating agents in this invention. The agricultural chemical composition of this invention may further incorporate therein a pH adjusting agent, inorganic salts, a thickener, etc. if desired.

By using (a) the compound of the general formula (I) of this invention in combination with (c) the surfactant other than (a) the compound, the amount of (a) the compound of the general formula (I) to be used can be decreased and, at the same time, the effect of (a) the compound of the general formula (I) in enhancing the efficacy of an agricultural chemical can be retained. As (c) the surfactant, a nonionic surfactant, an anionic surfactant, a cationic surfactant, an amphoteric surfactant, or any of the mixtures thereof may be used.

Examples of the nonionic surfactant include polyoxyethylene alkyl ethers, polyoxyethylene alkyl aryl ethers, polyoxyethylene alkyl aryl ether-formaldehyde condensates, polyoxyalkylene aryl ethers, polyoxyalkylene alkyl esters, polyoxyalkylene alkyl sorbitol esters, polyoxyalkylene sorbitan esters, polyoxyalkylene alkyl glycerol esters, polyoxyalkylene block copolymers, polyoxyalkylene block copolymer alkyl glycerol esters, polyoxyalkylene alkyl sulfon amides, polyoxyalkylene rosin esters, polyoxypropylene block copolymers, polyoxyethylene oleyl ethers, polyoxyalkylene alkyl phenols, alkyl glycosides, alkyl polyglycosides, and polyoxyalkylene alkyl polyglycosides, and mixtures of two or more of them.

Examples of the cationic surfactant include monoalkyl di-lower alkylamines, dialkyl mono-lower alkylamines, alkylamine ethylene oxide adducts, and alkylamine propylene oxide adducts such as, for example, tallow amine ethylene oxide adduct, oleyl amine ethylene oxide adduct, soyamine ethylene oxide adduct, and cocoamine ethylene oxide adduct, synthetic alkylamine ethylene oxide adducts, octylamine ethylene oxide adducts, quaternized products thereof (such as, for example, quaternized products with methyl chloride, dimethyl sulfuric acid, diethyl sulfuric acid, and benzyl chloride), and mixtures thereof.

The anionic surfactants are typically available as aqueous solutions or solids. Examples of such anionic surfactants include sodium mono- and dialkylnaphthalenesulfonates, sodium alpha-olefinsulfonates, sodium alkanesulfonates, alkylsulfosuccinates, alkylsulfates, polyoxyalkylene alkyl ether sulfates, polyoxyalkylene alkyl aryl ether sulfates, polyoxyalkylene styryl phenyl ether sulfates, mono- and dialkylbenzenesulfonates, alkylnaphthalenesulfonates, alkylnaphthalenesulfonate/formaldehyde condensates, alkyl diphenyl ether sulfonates, olefinic sulfonates, mono- and dialkylphosphates, polyoxyalkylene mono- and di-alkyl ether phosphates, polyoxyalkylene mono- and di-phenyl ether phosphates, polyoxyalkylene mono- and di-alkylphenyl ether phosphates, polycarboxylates, linear and branched alkyl amide polyoxyalkylene ether carboxylic acids and salts thereof, alkyl polyoxyalkylene ether carboxylates other than those of this invention, alkenyl polyoxyalkylene ether carboxylates other than those of this invention, fatty acids or salts thereof such as, for example, caprylic acid and salts thereof, lauric acid and salts thereof, stearic acid and salts thereof, and oleic acid and salts thereof, and N-methyl fatty acid taurides, and mixtures of two or more of them (including sodium, potassium, ammonium, and amine salts).

Examples of the appropriate amphoteric surfactants include lauryl dimethyl amine oxide, Armox C/12, amine oxides, Monaterics, Miranols, betaine, Lonzaines, other amine oxides, and mixtures thereof.

In all of these surfactants, nonionic surfactants prove to be particularly advantageous. In the efficacy enhancing composition for agricultural chemicals which includes the compound of the general formula (I) mentioned above and a surfactant other than the compound of general formula (I) as active components, the mixing ratio by weight of the compound of the general formula (I) to the surfactant other than the compound of general formula (I), [the total amount of the compound of the general formula (I)]/[the amount of the surfactant other than the compound of general formula (I)], is in the range of 1/10 to 30/1, preferably 1/5 to 10/1.

The agricultural chemical composition of the present invention comprises an efficacy enhancer for agricultural chemicals as described above, and an agricultural chemical. In the agricultural chemical composition of this invention, the weight ratio of (a) the compound of the general formula (I) in the efficacy enhancer for agricultural chemicals or the efficacy enhancing composition for agricultural chemicals to the agricultural chemical, [the compound of the general formula (I)]/[the agricultural chemical], is in the range of 0.03–50, preferably 0.04–20, and more preferably 0.1–10. If this ratio is less than 0.03, the effect in enhancing the efficacy of the agricultural chemical will not be fully satisfied. Conversely, if this ratio exceeds 50, the excess will not be expected to bring about a proportionate addition to the effect.

The agricultural chemical composition of the present invention is not limited to any formulation. It may be used in the form of emulsifiable concentrate (emulsion), wettable powder(water dispersible powder), granules, dust, flowable powder, or liquid. It, therefore, may further incorporate therein such additives as, for example, an emulsifier, a dispersant, and a carrier, depending on the form of aggregation. For the actual use of the efficacy enhancer for agricultural chemicals of this invention, a method for using an agricultural chemical composition already containing the efficacy enhancer for agricultural chemicals and formulated in advance in a varying form mentioned above and a method for putting to use the efficacy enhancer for agricultural chemicals prepared in advance separately of agricultural chemical at the time that the agricultural chemical (not containing the efficacy enhancer of this invention) is diluted prior to use are available. By either of these methods, the efficacy enhancer of this invention is enabled to manifest the effect aimed at.

By allowing the agricultural chemical composition of the present invention to incorporate a chelating agent additionally therein, the efficacy of the agricultural chemical is dramatically increased.

Examples of the pH adjusting agent to be used in this invention include citric acid, phosphoric acid (pyrophosphoric acid), gluconic acid, and salts thereof.

The inorganic salts which can be used in this invention include such inorganic mineral salts as, for example, inorganic salt clay, talc, bentonite, zeolite, calcium carbonate, diatomaceous earth, and white carbon and such inorganic ammonium salts as, for example, ammonium sulfate, ammonium nitrate, ammonium phosphate, ammonium thiocyanate, ammonium chloride, and ammonium sulfamate.

As a thickener for the present invention, any of natural, semisynthetic, and synthetic water-soluble thickeners can be used. Examples of the natural thickener include xanthan gum and xanflow of microorganic origins and pectin, gum arabic, and guayule rubber of plant origins. Examples of the semisynthetic thickener include methylated products, carboxyalkylated products, and hydroxyalkylated products of cellulose or starch derivatives (including methyl cellulose, carboxymethyl cellulose, and hydroxymethyl cellulose), and sorbitol. Examples of the synthetic thickener include polyacrylates, polymaleates, polyvinyl pyrrolidone, and pentaerythritol ethylene oxide adduct.

Examples of the agricultural chemicals which are usable in the agricultural chemical compositions contemplated by the present invention will be cited below. It should be noted, however, that other agricultural chemicals are also available.

Examples of the bactericide(or fungicide) include Dithane (zinc ethylenebis(dithiocarbamate)), Maneb (manganese ethylenebis(dithiocarbamate)), Thiram (bis (dimethylthiocarbamoyl) disulfide), Manzeb (complex of zinc and manganese ethylenebis(dithiocarbamate)), Bisdithane (bisdimethyl dithiocarbamoyl zinc ethylene bisdithiocarbamate), and Propineb (polymeric zinc propylenebis(dithiocarbamate)), benzimidazole-based bactericides including Benomyl (methyl 1-(butylcarbamoyl)-2-benzimidazole carbamate) and Thiophanate-methyl (dimethyl(4,4'-o-phenylenebis(3-thioallophanate)), and Vinclozolin (3-(3,5-dichlorophenyl)-5-methyl-5-vinyl-1,3-oxazolidine-2,4-dione), Iprodione (3-(3,5-dichlorophenyl)-N-isopropyl-2,4- dioxoimidazolidine-1-carboxamide), Procymidone (N-(3,5-dichlorophenyl)-1,2-dimethylcyclopropane-1,2-dicarboximide), Anilazine (2,4-dichloro-6-(o-chloroanilino)-1,3,5-triazine), Triflumizole ((E)-4-chloro-α, α, α-trifluoro-N-(1-imidazol-1-yl-2-propoxyethylidene)o-toluidine), Metalaxyl (methyl-N-(2-methoxyacetyl)-N-(2,6-xylyl)-DL-alaninate), Bitertanol (all-rac-1-(biphenyl-4-yloxy)-3,3-dimethyl-1-(1,2,4-triazol-1-yl)butan-2-ol), Pyrifenox (2', 4'-dichloro-2-(3-pyridyl) acetophenone-(EZ)-O-methyloxime), Fenarimol (2,4'-dichloro-α-(pyrimidin-5-yl)benzhydrylalcohol), Triforine (1,4-bis-(2,2,2 -trichloro-1-formamidoethyl)-piperazine), Guazatine iminoctadine (1,1-iminiodi(octamethylene) diguanidinium triacetate), Oxine-copper, antibiotic bactericides (streptomycin type, tetracycline type, polyoxins type, blasticidin S type, kasugamycin type, and validamycin type), Triadimefon (1-(4-chlorophenoxy)-3,3-dimethyl-1-(1,2,4-triazol-1-yl)-2-butanone), Isoprothiolane (diisopropyl-1,3-dithiolan-2-ylidenemalonate), Daconil (tetrachloroisophthalonitrile), Pansoil (5-ethoxy-3-trichloromethyl-1,2,4-thiadiazole), Fthalide (4,5,6,7-tetrachlorophthalide), Kitazin-P (0,0-diisopropyl-phosphorothioate), Hinosan (ethyl S,S-diphenylphosphorodithioate), Probenazole (3-allyloxy-1,2-benzisothiazol 1,1 -dioxide), Captan (N-(trichloromethylthio)-4-cyclohexene-1,2-dicarboximide), and Fosetyl (aluminum tris(ethylphosphonate)).

In the case of the insecticides, the pyrethroid type insecticides include Fenvalerate (α-cyano-3 -phenoxybenzyl-2-(4-chlorophenyl)-3-methylbutanoate) and Baythroid (cyano-4-fluoro-3-phenoxybenzyl-3-(2,2-dichlorovinyl)-2,2-dimethylcyclopropanecarboxylate), organic phosphorus type insecticides include DDVP (2,2-dichlorovinyldimethyl phosphate), Sumithion (MEP) (dimethyl 4-nitro-m-tolyl phosphorothioate), Malathion (S-1,2-bis(ethoxycarbonyl) ethyldimethyl phosphorodethioate), Dimethoate (dimethyl S-(N-methylcarbamoylmethyl) phosphorodithioate), Elsan (S-[α-(ethoxycarbonyl)benzyl] dimethyl phosphorodithioate), and Baycid (dimethyl 4-methylthio-m-tolyl phosphorothioate), carbamate type insecticides include Bassa (0-sec-butylphenyl methylcarbamate), MTMC (m-tolylmethylcarbamate), Meopal (3,4-dimethylphenyl-N-methylcarbamate), and NAC (1-naphthyl methylcarbamate), and Methomyl (S-methyl-N-(methylcarbamoyloxy) thioacetimidate), and Cartap (S,S'-2-dimethylamino trimethylene bis-(thiocarbamate)), for example.

Examples of the natural insecticide include pyrethrin preparations and piperonyl butoxide preparations which originate from Chrysanthemum cinerariaefolium, rotenone preparations, which originate from Derris which is a shrub of the pulse family, and nicotine (3-(1-methyl-2-pyrrolidinyl)pyridine sulfate) preparations originating in derris shrubs of Family Leguminosae. Examples of the insect growth regulators (IGR), Diflubenzuron (1-(4-chlorophenyl)-3-(2,6-difluorobenzoyl) urea), Teflubenzuron (1-(3,5-dichloro-2,4-difluorophenyl)-3-(2,6- difluorobenzoyl) urea), Chlorfluazuron (1-[3,5-dichloro-4-(3-chloro-5-trifluoromethyl-2-pyridiloxyphenyl]-3-(2,6-difluorobenzoyl) urea, Buprofezin (2-tert butylimino-3-isopropyl-5-phenyl-3,4,5,6-tetrahydro-2H-1,3,5-thiadiazin-4-one), and Fenoxycarb (ethyl 2-(4-phenoxyphenoxy) ethylcarbamate).

Examples of the acaricide include Sumiito (2-tert-butyl-5-(4-tert-butylbenzylthio)-4-chloropyridazine-3-(2H)-one), Acricid (2,4-dinitro-6-sec.-butylphenyldimethylacrylate), Chloromite (isopropyl 4,4-dichlorobenzylate), Akar (ethyl 4,4'-dichlorobenzilate), Kelthane (2,2,2-trichloro-1,1-bis(p-chlorophenyl)ethanol), Citrazon (benzoic 3-chloro-N-ethoxy-2,6-dimethoxybenzimidic anhydride), Omite (2-(p-tert-butylphenoxy)cyclohexyl propyn-2-yl sulfite), Osadan (bis[tris(2-methyl-2-phenylpropyl)tin]oxide), Hexythiazox (trans-5-(4-chlorophenyl)-N-cyclohexyl-4-methyl-2-oxothiazolidine-3-carboxamide), and Amitraz (N,N-bis(2,4-xylyliminomethyl)methylamine).

Examples of the acid amide-based herbicide include Stam (3',4'-dichloropropionanilide, DCPA) and Alachlor (2-chloro-2',6'-diethyl-N-(methoxymethyl)-acetanilide). Examples of the urea-based herbicide include DCMU (3-(3,4-dichlorophenyl)-1,1-dimethylurea) and Rinuron (3-(3,4-dichlorophenyl)-1-methoxy-1-methylurea). Examples of the sulfonyl urea-based herbicide, Thifensulfuronmethyl (methyl-3-(4-methoxy-6-methyl-1,3,5-triazin-2-ylcarbamoylsulfamoyl)-2-tanoate) and Flazasulfuron (1-(4,6-dimethoxy pyrimidin-2-yl)-3-(3-trifluoromethyl-2-pyridylsulfonyl) urea). Examples of the dipyridyl-based herbicide include Paraquat dichloride (1,1'-dimethyl-4,4'-bipyridinium dichloride) and Diquat dibromide (6,7-dihydrodipyride[1,2-a:2',1'c]-pyrazinediium dibromide). Example of the diazine-based herbicide include Bromacil (5-bromo-3-sec-butyl-6-methyluracil). Examples of the S-triazine-based herbicide include Gesatop (2-chloro-4,6-bis(ethylamino)-1,3,5-triazine) and Simetryn (2,4-bis (ethylamino)-6-methylthio-1,3,5-triazine). An example of the nitrile-based herbicide include DBN (2,6-dichlorobenzonitrile). Examples of the dinitroaniline-based herbicide include Trifluralin (α, α, α-trifluoro-2,6-dinitro-N,N-dipropyl-p-toluidine). Examples of the carbamate-based herbicide include Thiobencarb (Saturn) (S-p-chlorobenzyl diethylthiocarbamate) and MCC (methyl-3,4-dichlorocarbanylate. An example of the diphenyl ether-based herbicide include NIP (2,4-dichlorophenyl-p-nitrophenyl ether). An example of the phenol-based herbicide include PCP (sodium pentachlorophenoxide). An example of the benzoic acid-based herbicide include MDBA (3,6-dichloro-2-methoxybenzoic acid dimethylamine salt). Examples of the phenoxy-based herbicide include 2,4-D sodium salt (sodium 2,4-dichlorophenoxyacetate) and Mapica ([4-chloro-o-toluyl)oxy]aceto-o-chloroanilide). Examples of the organic phosphorus-based herbicide include Glyphosate (N-(phosphonomethyl) glycinate), Bialaphos (sodium salt of L-2-amino-4-[(hydroxy)(methyl) phosphinoyl]-butylyl-L-alanyl-N-alanine), and Glufosinate (ammonium DL-homoalanin-4-yl(methyl) phosphinate). An example of the aliphatic group-based herbicide include TCA sodium salt (sodium trichloroacetate).

Among these herbicides, the dipyridyl-based herbicides and the organic phosphorus-based herbicides are preferred. Among them, the organic phosphorus-based herbicides are more preferred, and Bialaphos (sodium salt of L-2-amino-4-[hydroxy)(methyl)phosphinoyl]-butylyl-L-alanyl-N-alanine), Glufosinate (ammonium DL-homoalanin-4-yl (methyl) phosphinate), or Glyphosate (N-(phosphonomethyl) glycinate) are particularly preferred.

Examples of the plant-growth regulator include MH (hydrazide maleate), Ethrel (2-chloroethylphosphonic acid), UASTA, and Bialaphos.

The agricultural chemical composition of this invention may further contain one or more ingredients such as plant growth regulators other than those cited above, fertilizers, and antiseptics.

For bactericidal, insecticidal, miticidal (acaricidal), weeding (herbicidal), and plant growth-regulating purposes, this invention contemplates using the agricultural chemical composition which contains the efficacy enhancer of this invention for agricultural chemicals in 0.03–50 times, preferably 0.04–20 times, and more preferably 0.1–10 times the amount of the agricultural chemical.

Examples of the agricultural chemical preparation using the efficacy enhancer of this invention for agricultural chemicals include (a) an agricultural chemical preparation which comprises at least one kind of compound of the general formula (I) mentioned above and separate packets of an agricultural chemical composition, (b) an agricultural chemical preparation which comprises separate packets of a composition formed of at least one kind of compound of the general formula (I) mentioned above and at least one kind of surfactant other than the compound and separate packets of an agricultural chemical composition, (c) an agricultural chemical preparation which comprises separate packets of at least one kind of compound of the general formula (I) mentioned above, separate packets of at least one kind of surfactant other than the compound of general formula (I) and separate packets of an agricultural chemical composition, (d) an agricultural chemical preparation which comprises separate packets of a composition formed of at least one kind of compound of the general formula (I) and a chelating agent, and separate packets of an agricultural chemical composition, (e) an agricultural chemical preparation which comprises separate packets of a composition formed of at least one kind of compound of the general formula (I) mentioned above, separate packets of at least one kind of surfactant other than the compound of general formula (I), and separate packets of an agricultural chemical composition, and (f) an agricultural chemical preparation which comprises separate packets of a composition formed of at least one kind of compound of the general formula (I), at least one kind of surfactant other than the compound of general formula (I), and a chelating agent and separate packets of an agricultural chemical composition. The term "agricultural chemical composition" in the expression "separate packets of an agricultural chemical composition" means a composition comprising the agricultural chemical and components at an arbitrary ratio and assuming such form of aggregation as emulsifiable concentrate or wettable powder and differs from the agricultural chemical composition which comprises the efficacy enhancer of this invention for agricultural chemicals and the agricultural chemical. The contents of the separate packets impose no limit on the form of aggregation but vary with the type of application and the purpose of use.

EXAMPLES

Example 1

Various efficacy enhancing compositions for agricultural chemicals shown in Tables 2–4 (hereinafter referred to briefly as "active component") were prepared by using compounds shown in Table 1 and optionally using surfactants and chelating agents shown in Tables 2–4. The symbol —X— in the general formula (I) represents —O— (oxygen) unless othernise specified.

TABLE 1

| No. | $R_1$ | $A_1$ | $R_2$ | n | $R_3$ | $R_4$ | $R_5$ | $m_1 + m_2$ |
|---|---|---|---|---|---|---|---|---|
| ① | coconut alkyl | $C_2$ alkylene | $C_1$ alkylene | 4.5 | coconut alkyl | $(CH_2CH_2O)_{m_1}H$ | $(CH_2CH_2O)_{m_2}H$ | 2 |
| ② | | | | | lauryl | $(CH_2CH_2O)_{m_1}H$ | $(CH_2CH_2O)_{m_2}H$ | 10 |
| ③ | | | | | $C_{14-18}$ alkyl | $C_{14-18}$ alkyl | $(CH_2CH_2O)_{m_2}H$ | 4 |
| ④ | $C_{12-15}$ alkyl | $C_2$ alkylene | $C_1$ alkylene | 6 | coconut alkyl | $(CH_2CH_2O)_{m_1}H$ | $(CH_2CH_2O)_{m_2}H$ | 2 |
| ⑤ | | | | | lauryl | $(CH_2CH_2O)_{m_1}H$ | $(CH_2CH_2O)_{m_2}H$ | 20 |
| ⑥ | | | | | tallow alkyl | $*[(EO)_{a_1}(PO)_{b_1}]H$ | $*[(EO)_{a_2}(PO)_{b_2}]H$ | — |
| ⑦ | | | | | $C_{18}$ alkyl | $C_{18}$ alkyl | $(CH_2CH_2O)_{m_2}H$ | 10 |
| ⑧ | $C_{11}$ alkyl | $C_2$ alkylene | $C_1$ alkylene | 3 | $C_{12}$ alkyl | $(CH_2CH_2O)_{m_1}H$ | $(CH_2CH_2O)_{m_2}H$ | 10 |
| ⑨ | | | | | $C_{12-14}$ alkyl | $(CH_2CH_2O)_{m_1}H$ | $(CH_2CH_2O)_{m_2}H$ | 20 |
| ⑩ | $C_9H_{19}$—⟨phenyl⟩ | $C_2$ alkylene | $C_1$ alkylene | 7 | $C_{12}$ alkyl | $C_{12}$ alkyl | $[CH(CH_3)CH_2O]_{m_2}H$ | 3 |
| ⑪ | | | | | $C_{12-14}$ alkyl | $C_{12-14}$ alkyl | $[CH(CH_3)CH_2O]_{m_2}H$ | 15 |
| ⑫ | $C_{13}$ alkyl | $C_3$ alkylene | $C_1$ alkylene | 15 | $C_{12-14}$ alkyl | $(CH_2CH_2O)_{m_1}H$ | $(CH_2CH_2O)_{m_2}H$ | 25 |
| ⑬ | $C_{18}$ alkyl | $C_3$ alkylene | $C_1$ alkylene | 15 | tallow alkyl | $(CH_2CH_2O)_{m_1}H$ | $(CH_2CH_2O)_{m_2}H$ | 15 |

*In Table 1, EO represents ethylene oxide and PO represents propylene oxide. EO and PO were added in such amounts as to satisfy $a_1 + a_2 = 2$ and $b_1 + b_2 = 4$ on the average.

TABLE 2

| Active component No. | Compound No. (a) | Surfactant (c) and/or chelating agent (b) used in combination | Weight ratio of (a)/(c)/(b) |
|---|---|---|---|
| Products of the invention | | | |
| 1 | ① | — | 100/0/0 |
| 2 | ① | POE (10) Nonylphenyl ether | 80/20/0 |
| 3 | ① | Potassium oxalate | 85/0/15 [(a)/(b) mol ratio = 1/0.97] |
| 4 | ② | — | 100/0/0 |
| 5 | ② | POE (20) Sorbitan monooleate | 80/20/0 |
| 6 | ② | *POE (6) Tallow fatty acid glycerol ester **EDTA.4Na | 75/*10/**15 [(a)/(b) mol ratio = 1/0.64] |
| 7 | ③ | — | 100/0/0 |
| 8 | ③ | POE (20) Sodium lauryl ether sulfate | 70/30/0 |
| 9 | ③ | POE (8) Oleyl ether | 50/50/0 |
| 10 | ④ | — | 100/0/0 |
| 11 | ④ | POE (20) Sorbitan monolaurate | 80/20/0 |
| 12 | ④ | Potassium oxalate | 85/0/15 [(a)/(b) mol ratio = 1/1.07] |
| 13 | ⑤ | — | 100/0/0 |
| 14 | ⑤ | Trimethyl monolauryl ammonium chloride | 80/20/0 |
| 15 | ⑤ | *POE (20) Lauryl ether **sodium gluconate | 80/*10/**10 [(a)/(b) mol ratio = 1/0.93] |

TABLE 3

| Active component No. | Compound No. (a) | Surfactant (c) and/or chelating agent (b) used in combination | Weight ratio of (a)/(c)/(b) |
|---|---|---|---|
| Products of the invention | | | |
| 16 | ⑥ | — | 100/0/0 |
| 17 | ⑥ | POE (18) Glycerin palm fatty acid ester | 65/35/0 |
| 18 | ⑥ | Cysteine | 95/0/5 [(a)/(b) mol ratio = 1/0.63] |
| 19 | ⑦ | — | 100/0/0 |
| 20 | ⑦ | Lauryl dimethylamine oxide | 60/40/0 |
| 21 | ⑦ | NTA | 80/0/20 [(a)/(b) mol ratio = 1/1.51] |
| 22 | ⑧ | — | 100/0/0 |
| 23 | ⑧ | Dimethyl didecyl ammonium chloride | 80/20/0 |
| 24 | ⑧ | POE (10) Oleyl ether | 80/20/0 |
| 25 | ⑨ | — | 100/0/0 |
| 26 | ⑨ | POE (7) Secondary-$C_{12-13}$ ether | 50/50/0 |

TABLE 3-continued

| Active component No. | Compound No. (a) | Surfactant (c) and/or chelating agent (b) used in combination | Weight ratio of (a)/(c)/(b) |
|---|---|---|---|
| 27 | ⑨ | *POE (20) Lauryl sulfuric acid triethanol amine **sodium heptoate | 45/*45/**10 [(a)/(b) mol ratio = 1/5.8] |
| 28 | ⑩ | — | 100/0/0 |
| 29 | ⑩ | POE (10) Oleic acid ester | 90/10/0 |
| 30 | ⑩ | POE (8) Oleyl ether | 70/30/0 |

TABLE 4

| Active component No. | Compound No. (a) | Surfactant (c) and/or chelating agent (b) used in combination | Weight ratio of (a)/(c)/(b) |
|---|---|---|---|
| Products of the invention | | | |
| 31 | ⑪ | — | 100/0/0 |
| 32 | ⑪ | POE (10) Nonylphenyl ether | 90/10/0 |
| 33 | ⑪ | EDTA.4Na | 80/0/20 [(a)/(b) mol ratio = 1/1.24] |
| 34 | ⑫ | — | 100/0/0 |
| 35 | ⑫ | *POE (7) Secondary-$C_{12-13}$ ether | 70/30/0 |
| 36 | ⑫ | *POE (7) Secondary-$C_{12-13}$ ether/**potassium oxalate | 80/*10/**10 [(c)/(b) mol ratio = 1/1.75] |
| 37 | ⑬ | — | 100/0/0 |
| 38 | ⑬ | POE (8) Tallow fatty acid glycerol ester | 70/30/0 |
| 39 | ⑬ | *POE (10) Tallow fatty acid glycerol ester/ **sodium heptoate | 45/*45/**10 [(a)/(b) mol ratio = 1/1.7] |
| Comparative product | | | |
| 40 | | POE (10) Sodium Lauryl ether acetate | 100/0/0 |
| 41 | | POE (6) Sodium $C_{12-15}$ ether acetate | 100/0/0 |
| 42 | | POE (3) Potassium oleyl ether acetate | 100/0/0 |

The components mentioned above were each dissolved in deionized water to obtain a dilute solution containing the active component at a concentration of 600 ppm. Three kinds of agricultural chemical compositions per active component were obtained by diluting three commercially available herbicides, namely Touchdown Liquid (containing 38% by weight of Trimethylsulfonium glyphosate as an active component), Basta Liquid (containing 18.5% by weight of Glufosinate as an active component), and Prigrox L Liquid (containing 12% by weight of a mixture of Diquat dibromide with Paraquat dichlorides as an active component), with the dilute solution so as to have active component concentrations respectively of 1900 ppm, 925 ppm, and 1200 ppm.

For a hothouse experiment, seeds of Barnyardgrass were sown and germinated in pots, 12 cm in inside diameter, each filled with the soil prepared by mixing fertile soil taken from paddy field, river sand, and commercially available culture soil at a weight ratio of 7:2:1. To heighten individual uniformity among these pots, the pots incurring abnormal growth of the weed were discarded. The pots in which the weed grew to a height of about 35 cm were adopted for the test. The agricultural chemical compositions were applied uniformly to the weed in the pots by the use of a spray gun (produced by Iwata Tosoki Kogyo K.K. and marketed under product code of "RG Type") at the rates of 5 liters of Touchdown Liquid and 10 liters each of Basta Liquid and Prigrox L Liquid per are to rate the herbicidal effect.

The herbicidal effect was ratedcby weighing the aerial (above-ground) parts of the weed in the relevant pots performing calculation of the following formula using the resultant fresh weights in comparison with the fresh weights of the aerial parts of weed in the untreated plot.

Herbicidal ratio=[(Fresh weight of aerial parts (g) in untreated plot)−(Fresh weight of aerial parts (g) in treated plot)]/(Fresh weight of aerial parts (g) in untreated plot)×100 (%)

The herbicidal ratios of the agricultural chemical compositions consequently found are shown in Tables 5 and 6.

TABLE 5

| | Diquat dibromide with | | |
|---|---|---|---|
| Active component No. | Herbicidal ratio (%) | | |
| | Touchdown Liquid | Basta Liquid | Prigrox L Liquid |
| Product of the invention | | | |
| 1 | 90.8 | 92.4 | 93.1 |
| 2 | 96.1 | 95.2 | 95.8 |
| 3 | 98.5 | 98.8 | 99.4 |
| 4 | 96.4 | 97.2 | 97.2 |
| 5 | 93.3 | 90.2 | 94.2 |
| 6 | 92.6 | 91.1 | 92.2 |
| 7 | 89.4 | 92.2 | 94.4 |
| 8 | 89.2 | 93.1 | 95.6 |
| 9 | 90.0 | 92.8 | 96.0 |
| 10 | 89.8 | 90.2 | 91.4 |
| 11 | 88.9 | 92.3 | 94.0 |
| 12 | 96.8 | 99.0 | 99.5 |
| 13 | 92.3 | 94.6 | 91.2 |
| 14 | 94.2 | 93.8 | 93.4 |
| 15 | 93.5 | 92.4 | 94.6 |
| 16 | 90.5 | 89.5 | 93.0 |
| 17 | 90.4 | 92.4 | 88.4 |
| 18 | 90.3 | 92.2 | 90.3 |
| 19 | 89.4 | 94.0 | 96.0 |
| 20 | 93.2 | 94.6 | 96.2 |
| 21 | 91.5 | 93.5 | 92.9 |

TABLE 6

| Active component No. | Herbicidal ratio (%) | | |
|---|---|---|---|
| | Touchdown Liquid | Basta Liquid | Prigrox L Liquid |
| Product of the invention | | | |
| 22 | 92.2 | 90.3 | 95.3 |
| 23 | 90.8 | 94.2 | 96.1 |
| 24 | 93.4 | 95.1 | 94.3 |
| 25 | 90.5 | 95.3 | 90.8 |
| 26 | 89.8 | 95.5 | 96.2 |
| 27 | 92.2 | 90.8 | 96.0 |
| 28 | 94.0 | 91.3 | 92.4 |
| 29 | 93.5 | 92.3 | 94.3 |
| 30 | 94.0 | 90.4 | 94.5 |
| 31 | 90.3 | 96.0 | 98.0 |
| 32 | 92.1 | 97.0 | 97.2 |
| 33 | 94.0 | 92.3 | 98.6 |
| 34 | 92.2 | 92.0 | 94.3 |
| 35 | 96.0 | 93.0 | 95.5 |
| 36 | 91.5 | 92.5 | 97.2 |
| 37 | 89.9 | 94.0 | 96.0 |
| 38 | 90.3 | 96.0 | 97.5 |
| 39 | 93.0 | 92.4 | 98.0 |
| Comparative product | | | |
| 40 | 70.5 | 78.4 | 85.4 |
| 41 | 81.2 | 72.6 | 82.2 |

TABLE 6-continued

| Active component No. | Herbicidal ratio (%) | | |
|---|---|---|---|
| | Touchdown Liquid | Basta Liquid | Prigrox L Liquid |
| 42 | 85.2 | 80.0 | 79.5 |
| No addition | 59.3 | 68.2 | 73.0 |

*In the untreated plot, the plant grew in normal condition throughout the entire test period.

Example 2

Female adult acari of Tetranychus kanzawai kishida were planted onto kidney bean leaf disks at a ratio of 30 imagines per lot on three runs and then incubated at 25° C. for 24 hours. Subsequently, the whole leaf disks were dipped in a test solution for 5 seconds. After taking out of the test solution and allowing to stand at 25° C. for 48 hours, the leaf disks were observed and the acaricidal ratios were determined on the basis of the result in the untreated plot (refer to the following equation). As acaricides, Nissorun Wettable Powder (containing 10% by weight of Hexythiazox as an active component) and Osadan Wettable Powder (containing 25% by weight of Fenbutatin oxide as an active component) diluted each to 2000 times the original volume and the same efficacy enhancer for agricultural chemicals as used in Example 1 were adopted. They were combined so that the resultant preparations contained the active component of the efficacy enhancer at a concentration of 0.1% by weight. Other preparations omitting the incorporation of the efficacy enhancer were similarly adopted. The results are shown in Tables 7 and 8.

Acaricidal ratio=[(Number of surviving mites in untreted plot)−(number of surviving mites in treated plot)]/(number of surviving mites in untreated plot)×100 (%)

TABLE 7

| Active component No. | Acaricidal ratio (%) | |
|---|---|---|
| | Nissorun Wettable Powder | Osadan Wettable Powder |
| Product of the invention | | |
| 1 | 86.7 | 80.0 |
| 2 | 93.3 | 93.3 |
| 3 | 100.0 | 100.0 |
| 4 | 83.3 | 90.0 |
| 5 | 93.3 | 100.0 |
| 6 | 80.0 | 93.3 |
| 7 | 86.7 | 83.3 |
| 8 | 86.7 | 76.7 |
| 9 | 90.0 | 86.7 |
| 10 | 80.0 | 93.3 |
| 11 | 93.3 | 100.0 |
| 12 | 100.0 | 100.0 |
| 13 | 76.7 | 76.7 |
| 14 | 83.3 | 73.3 |
| 15 | 80.0 | 80.0 |
| 16 | 80.0 | 83.3 |
| 17 | 93.3 | 96.7 |
| 18 | 90.0 | 93.3 |
| 19 | 96.7 | 83.3 |
| 20 | 80.0 | 80.0 |
| 21 | 93.3 | 76.7 |

TABLE 8

| Active component No. | Acaricidal ratio (%) | |
|---|---|---|
| | Nissorun Wettable Powder | Osadan Wettable Powder |
| Product of the invention | | |
| 22 | 86.3 | 80.0 |
| 23 | 80.0 | 76.7 |
| 24 | 96.7 | 93.3 |
| 25 | 80.0 | 83.3 |
| 26 | 76.7 | 80.0 |
| 27 | 83.3 | 80.0 |
| 28 | 80.0 | 83.3 |
| 29 | 96.7 | 93.3 |
| 30 | 96.7 | 96.7 |
| 31 | 76.7 | 80.0 |
| 32 | 80.0 | 80.0 |
| 33 | 80.0 | 83.3 |
| 34 | 83.3 | 76.7 |
| 35 | 96.7 | 76.7 |
| 36 | 96.7 | 80.0 |
| 37 | 83.3 | 80.0 |
| 38 | 80.0 | 76.7 |
| 39 | 83.3 | 83.3 |
| Comparative product | | |
| 40 | 63.3 | 56.3 |
| 41 | 60.0 | 63.3 |
| 42 | 66.7 | 60.0 |
| No addition | 53.3 | 46.7 |

Example 3

(I) Rice planthopper larvas of the third year were incubated and adopted for testing the efficacy of the insecticide by the dipping method using 10 heads per plot on the three-replication system. The insecticidal ratio was determined in the same manner as the acaricidal ratio. Sumithion Emulsifiable Concentrate (containing 50% by weight of MEP as an active component) and Agrothrin Wettable Powder (containing 6% by weight of Dipermethrin as an active component), as commercially available insecticides, were each diluted to 2000 times the original volume. The dilute solutions thus obtained and the same efficacy enhancer as used in Example 1 were combined to obtain preparations containing the efficacy enhancer at a concentration of 0.1% by weight.

(2). Leaf disks of kidney beans were wholly immersed in a test solution for 5 seconds, taken out of the test solution, and air-dried. The larvas of leafhoppers were planted 10 heads each on the leaf disks and nursed at 25° C. for 10 days. Then, the leaf disks were visually examined to take count of destroyed leafhoppers and determine the efficacy of the insecticides. The test was performed on the three-replication system. The insecticidal ratio was determined in the same manner as the acaricidal ratio. Dimilin Wettable Powder (containing 23.5% by weight of Diflubenzuron as an active component), as a commercially available insecticide, was diluted to 2000 times the original volume. The dilute solution thus obtained and the same efficacy enhancer as used in Example 1 were combined to obtain preparations containing the efficacy enhancer at a concentration of 0.1% by weight.

The results are shown in Tables 9 and 10.

TABLE 9

| Active component No. | Insecticidal ratio (%) | | |
|---|---|---|---|
| | Sumithion Emulsifiable Concentrate | Agrothrin Emulsifiable Concentrate | Dimilin Wettable Powder |
| Product of the invention | | | |
| 1 | 66.7 | 73.3 | 70.0 |
| 2 | 86.7 | 93.3 | 93.3 |
| 3 | 100.0 | 96.7 | 100.0 |
| 4 | 70.0 | 76.7 | 76.7 |
| 5 | 73.3 | 73.3 | 80.0 |
| 6 | 70.0 | 80.0 | 80.0 |
| 7 | 76.7 | 76.7 | 70.0 |
| 8 | 80.0 | 70.0 | 76.7 |
| 9 | 80.0 | 80.0 | 80.0 |
| 10 | 80.0 | 80.0 | 83.3 |
| 11 | 93.3 | 96.7 | 93.3 |
| 12 | 100.0 | 100.0 | 96.7 |
| 13 | 76.7 | 76.7 | 70.0 |
| 14 | 83.3 | 80.0 | 76.7 |
| 15 | 76.7 | 83.3 | 80.0 |
| 16 | 80.0 | 70.0 | 76.7 |
| 17 | 90.0 | 93.3 | 90.0 |
| 18 | 76.7 | 80.0 | 80.0 |
| 19 | 83.3 | 76.7 | 80.0 |
| 20 | 76.7 | 73.3 | 83.3 |
| 21 | 76.7 | 83.3 | 83.3 |

TABLE 10

| Active component No. | Insecticidal ratio (%) | | |
|---|---|---|---|
| | Sumithion Emulsifiable Concentrate | Agrothrin Emulsifiable Concentrate | Dimilin Wettable Powder |
| Product of the invention | | | |
| 22 | 80.0 | 76.7 | 80.0 |
| 23 | 76.7 | 73.3 | 80.0 |
| 24 | 96.7 | 93.3 | 96.7 |
| 25 | 76.7 | 73.3 | 73.3 |
| 26 | 76.7 | 70.0 | 76.7 |
| 27 | 70.0 | 80.0 | 80.0 |
| 28 | 83.3 | 83.3 | 80.0 |
| 29 | 96.7 | 93.3 | 96.7 |
| 30 | 93.3 | 93.3 | 96.7 |
| 31 | 83.3 | 87.6 | 70.0 |
| 32 | 86.7 | 70.0 | 70.0 |
| 33 | 76.7 | 73.3 | 80.0 |
| 34 | 80.0 | 83.3 | 80.0 |
| 35 | 93.3 | 96.7 | 96.7 |
| 36 | 96.7 | 96.7 | 93.3 |
| 37 | 83.3 | 83.3 | 80.0 |
| 38 | 70.0 | 80.0 | 76.7 |
| 39 | 76.7 | 70.0 | 73.3 |
| Comparative product | | | |
| 40 | 66.7 | 56.7 | 66.7 |
| 41 | 60.0 | 56.7 | 60.0 |
| 42 | 56.7 | 60.0 | 66.7 |
| No addition | 46.7 | 40.0 | 53.3 |

Example 4

A spore suspension of ($10^7$/ml) of cucumber Botrytis cinerea acquiring the resistance against fungicides was applied to young cucumber seedlings at the trifoliate stage in a dose of 10 ml per pot and the resulting seedlings were allowed to stand at 25° C. and 90% RH for one day.

Benlate Wettable Powder (containing 50% by weight of Benomyl as an active component), a commercially available bactericide, was 2000 times diluted with a 2500 times solution of the effective matter used in Example 1. The resultant dilute solution was sprayed 5 ml per pot. The treated cucumbers were left standing at 25° C. and 85% RH and visually examined to take count of disease spots and determine the bactericidal ratio based on the data obtained in the untreated plot. The results are shown in Tables 11 and 12.

Bactericidal ratio=1−[(Number of disease spots in treated plot)/(number of disease spots in untreated plot)]×100

TABLE 11

| Active component No. | Bactericidal ratio Benlate Wettable Powder |
|---|---|
| Product of the invention | |
| 1 | 83.3 |
| 2 | 96.2 |
| 3 | 100.0 |
| 4 | 79.4 |
| 5 | 93.4 |
| 6 | 90.0 |
| 7 | 83.3 |
| 8 | 93.2 |
| 9 | 90.4 |
| 10 | 85.6 |
| 11 | 95.4 |
| 12 | 98.8 |
| 13 | 93.3 |
| 14 | 97.2 |
| 15 | 86.4 |
| 16 | 90.0 |
| 17 | 98.5 |
| 18 | 92.3 |
| 19 | 86.3 |
| 20 | 84.2 |
| 21 | 89.3 |

TABLE 12

| Active component No. | Bactericidal ratio Benlate Wettable Powder |
|---|---|
| Product of the invention | |
| 22 | 90.3 |
| 23 | 92.1 |
| 24 | 96.4 |
| 25 | 89.2 |
| 26 | 88.3 |
| 27 | 79.8 |
| 28 | 84.6 |
| 29 | 96.4 |
| 30 | 98.2 |
| 31 | 79.4 |
| 32 | 83.3 |
| 33 | 86.4 |
| 34 | 89.4 |
| 35 | 98.2 |
| 36 | 99.7 |
| 37 | 83.4 |
| 38 | 87.4 |
| 39 | 86.3 |
| Comparative product | |
| 40 | 63.9 |
| 41 | 68.8 |
| 42 | 70.0 |
| No addition | 54.3 |

Examples 1–4 show the results of the comparison between the efficacy enhancers of this invention and the sodium salt and potassium salt of alkyl polyoxyalkylene ether carboxylic acids as comparative efficacy enhancers (comparative product) as to the effect. It is clearly noted from Tables 5–12 that the efficacy enhancers according to this invention manifested their effects conspicuously on a practical level, while the comparative enhancers enhanced the efficacy of agricultural chemicals to a slight but not practical level. It is clear, therefore, that the efficacy enhancers of this invention enhanced specifically the efficacy of agricultural chemicals as compared with the conventional sodium salt and potassium salt.

Example 5

The test of Example 1 was repeated, excepting Touchdown Liquid (containing 38% by weight of active component) as a herbicide and the active components 1, 4, and 28 of Example 1 as efficacy enhancers were used in the amounts shown in Table 13. The results are shown in Table 13.

TABLE 13

| Test No. | Active component | Concentration of herbicide (ppm) | Concentration of efficacy enhancer (ppm) | Weight ratio of agricultural chemical/efficacy enhancer | Herbicidal ratio (%) |
|---|---|---|---|---|---|
| 1 | Active compo- nent 1 | 3800 | 100 | 1/0.03 | 83.6 |
| 2 |  | 3800 | 500 | 1/0.13 | 88.4 |
| 3 |  | 3800 | 1000 | 1/0.26 | 92.3 |
| 4 |  | 3800 | 10000 | 1/2.63 | 97.0 |
| 5 |  | 3800 | 30000 | 1/7.89 | 98.2 |
| 6 |  | 3800 | 50000 | 1/13.16 | 89.4 |
| 7 |  | 3800 | 80000 | 1/21.05 | 90.2 |
| 8 | Active compo- nent 4 | 3800 | 100 | 1/0.03 | 79.9 |
| 9 |  | 3800 | 500 | 1/0.13 | 95.4 |
| 10 |  | 3800 | 1000 | 1/0.26 | 98.3 |
| 11 |  | 3800 | 10000 | 1/2.63 | 98.4 |
| 12 |  | 3800 | 30000 | 1/7.89 | 99.0 |
| 13 |  | 3800 | 50000 | 1/13.16 | 93.4 |
| 14 |  | 3800 | 80000 | 1/21.05 | 92.4 |
| 15 | Active compo- nent 28 | 3800 | 100 | 1/0.03 | 80.0 |
| 16 |  | 3800 | 500 | 1/0.13 | 95.4 |
| 17 |  | 3800 | 1000 | 1/0.26 | 97.6 |
| 18 |  | 3800 | 10000 | 1/2.63 | 98.0 |
| 19 |  | 3800 | 30000 | 1/7.89 | 98.5 |
| 20 |  | 3800 | 50000 | 1/13.16 | 91.6 |
| 21 |  | 3800 | 80000 | 1/21.05 | 92.0 |
| 22 | — | 3800 | 0 | — | 61.0 |

* In the untreated plot, the plant grew in normal condition throughout the entire test period.

Example 6

The test of (I) of Example 3 was repeated, excepting Sumithion Emulsifiable Concentrate (containing 50% by weight of MEP as an active component) as an insecticide and the active components 1 and 20 of Example 1 as efficacy enhancers were used in the amounts shown in Table 14. The results are shown in Table 14.

TABLE 14

| Test No. | Active component | Concentration of insecticide (ppm) | Concentration of efficacy enhancer (ppm) | Weight ratio of agricultural chemical/efficacy enhancer | Insecticidal ratio (%) |
|---|---|---|---|---|---|
| 1 | Active compo- nent 1 | 250 | 10 | 1/0.08 | 66.7 |
| 2 |  | 250 | 25 | 1/0.2 | 76.7 |
| 3 |  | 250 | 250 | 1/2 | 83.3 |
| 4 |  | 250 | 1000 | 1/8 | 100.0 |
| 5 |  | 250 | 2500 | 1/20 | 100.0 |
| 6 |  | 250 | 5000 | 1/40 | 100.0 |
| 7 | Active compo- nent 20 | 250 | 10 | 1/0.08 | 76.7 |
| 8 |  | 250 | 25 | 1/0.2 | 80.0 |
| 9 |  | 250 | 250 | 1/2 | 96.7 |

TABLE 14-continued

| Test No. | Active component | Concentration of insecticide (ppm) | Concentration of efficacy enhancer (ppm) | Weight ratio of agricultural chemical/efficacy enhancer | Insecticidal ratio (%) |
|---|---|---|---|---|---|
| 10 |  | 250 | 1000 | 1/8 | 100.0 |
| 11 |  | 250 | 2500 | 1/20 | 100.0 |
| 12 |  | 250 | 5000 | 1/40 | 100.0 |
| 13 | — | 250 | — | — | 46.7 |

Example 7

The compound 1 shown in Table 1, the potassium salt having the compound 1 as an anion moiety, and the triethanolamine salt (TEA salt) having the compound 1 as an anion moiety were tested for relation between concentration and viscosity. The viscosity was determined by preparing an aqueous solution containing the relevant compound at a concentration shown in Table 15, and measuring the viscosity of this aqueous solution with a B type viscosimeter (produced by Tokyo Keiki K.K.) using No. 2 rotor under the conditions of 60 rpm 20° C. The results are shown in Table 15.

TABLE 15

|  | Concentration of compound (% by weight) | | | |
|---|---|---|---|---|
|  | 20 | 50 | 80 | 100 |
| Viscosity (cP) |  |  |  |  |
| Compound 1 | 12.5 | 130 | 200 | 370 |
| Compound 1 - K salt | 135 | Gelated | Immeasurable | Immeasurable |
| Compound 1 - TEA salt | 78 | Gelated | Immeasurable | Immeasurable |

What is claimed is:

1. An agricultural chemical composition, comprising an agricultural chemical and a compound of the formula (I):

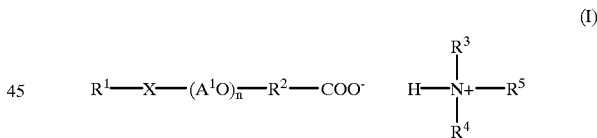

wherein X is —O—; $R^1$ is a linear or a branched alkyl group of 6–20 carbon atoms, or an alkylphenyl group containing an alkyl group of 6–18 carbon atoms; $R^2$ is an alkylene group of 1–4 carbon atoms; $R^3$, $R^4$ and $R^5$ are the same or different from each another and at least one of $R^3$, $R^4$ and $R^5$ is selected from the group consisting of a linear or a branched alkyl group of 6–30 carbon atoms and a linear or a branched alkenyl group of 6–30 carbon atoms and the remainder of $R^3$, $R^4$ and $R^5$ are selected from the group consisting of a benzyl group, hydrogen, and —$(A^2O)_m$—H; $A^1$ and $A^2$ are independently an alkylene group of 2–4 carbon atoms, n is a number of 1–30 on the average, and m is a number of 1–15 on the average.

2. The composition according to claim 1, which comprises (a) the compound of the formula (I) set forth in claim 1 and (b) 0.05 to 15 moles, per mole of the compound (a), of a chelating agent.

3. The composition according to claim 1, which comprises (a) the compound of the formula (I) set forth in claim 1, (c) at least one surfactant other than the compound of formula (I), and (b) 0.05 to 15 moles, per mole of the compound (a), of a chelating agent.

4. The composition as claimed in claim 3, wherein the surfactant is a non-ionic surfactant.

5. The composition as claimed in claim 3, wherein the weight ratio of (a) to (c) is in the range of 1:10 to 30:1.

6. The agricultural chemical composition according to claim 1, which comprises the compound of the formula (I) set forth in claim 1, and an agricultural chemical, the weight ratio of the compound of formula (I) to the agricultural chemical being in the range of 0.03:1 to 50:1.

7. The agricultural chemical composition as claimed in claim 6, wherein the agricultural chemical is a bactericide (or fungicide), an insecticide, an acaricide, a herbicide, or a plant-growth regulator.

8. The agricultural chemical composition as claimed in claim 6, wherein the agricultural chemical is a herbicide.

9. The agricultural chemical composition as claimed in claim 6, which further comprises (b) a chelating agent.

10. The agricultural chemical composition as claimed in claim 6, which further comprises (c) at least one surfactant other than the compound of the formula (I).

11. A method for enhancing the efficacy of agricultural chemicals, which comprises applying the composition set forth in claim 1 to a site will benefit from the treatment with the agricultural chemical.

12. The composition of claim 1, wherein $R^3$ is a linear or branched alkyl group of 6–30 carbon atoms or a branched alkenyl group of 6–30 carbon atoms, and $R^4$ and $R^5$ are independently —$(A^2O)_m$—H.

13. The composition of claim 1, wherein at least one of $R^3$, $R^4$ and $R^5$ is a coconut alkyl group.

14. The composition of claim 1, wherein at least one of $R^3$, $R^4$ and $R^5$ is a lauryl group.

15. The composition of claim 1, wherein at least one of $R^3$, $R^4$ and $R^5$ is a $C_{14}$ to $C_{18}$ alkyl group.

16. The composition of claim 1, wherein at least one of $R^3$, $R^4$ and $R^5$ is a tallow alkyl group.

17. The composition of claim 1, wherein at least one of $R^3$, $R^4$ and $P^5$ is a $C_{18}$ alkyl group.

18. The composition of claim 1, wherein at least one of $R^3$, $R^4$ and $R^5$ is a $C_{12}$ alkyl group.

19. The composition of claim 1, wherein at least one of $R^3$, $R^4$ and $R^5$ is a $C_{12}$–$C_{14}$ alkyl group.

20. The method according to claim 11, wherein the composition is applied to a plant or insect.

21. The agricultural chemical composition as claimed in claim 1, wherein the agricultural chemical is a bactericide (or fungicide), and insecticide, and acaricide, a herbicide, or a plant-growth regulator.

22. The agricultural chemical composition as claimed in claim 1, wherein the agricultural chemical is a herbicide.

23. The agricultural chemical composition as claimed in claim 1, which further comprises (b) a chelating agent.

24. The agricultural chemical composition as claimed in claim 1, which further comprises (c) at least one surfactant other than the compound of the formula (I).

25. The composition of claim 1, wherein the composition is in the form of an emulsion, a wettable powder, granules, dust, a flowable powder or a liquid.

26. The composition of claim 1, wherein the composition is an aqueous composition containing at least 20 wt % of a compound of formula (I).

* * * * *